United States Patent [19]

Pettit et al.

[11] Patent Number: 5,519,050
[45] Date of Patent: May 21, 1996

[54] ISOLATION AND STRUCTURAL ELUCIDATION OF HALISTATIN 3

[75] Inventors: George R. Pettit, Paradise Valley, Ariz.; Yoshitatsu Ichihara, Odawara, Japan

[73] Assignee: Arizona Board of Regents acting on behalf of Arizona State University, Tempe, Ariz.

[21] Appl. No.: 418,672

[22] Filed: Apr. 7, 1995

[51] Int. Cl.⁶ .................. A61K 31/335; C07D 315/00
[52] U.S. Cl. ........................... 514/450; 549/264
[58] Field of Search ................... 549/267, 264; 514/450

[56] References Cited

U.S. PATENT DOCUMENTS 5,328,929  7/1994  Pettit et al. .................. 514/462
5,352,804  10/1994  Pettit et al. .................. 549/264

*Primary Examiner*—C. Warren Ivy
*Assistant Examiner*—Amelia Owens
*Attorney, Agent, or Firm*—Richard R. Mybeck; Walter R. Mybeck, II

[57] ABSTRACT

The Micronesian marine sponge Phakellia sp. has been found to contain certain key members of the antineoplastic halichondrin/halistatin family. These compounds include halichondrin B, homohalichondrin B, halistatin 1, and halistatin 3.

Halistatin 3 is a newly discovered member of this family. It inhibited both the P388 leukemia cell line and selected brain, lung, colon, ovarian, renal, and melanoma type cancer cell lines with $ED_{50}/GI_{50}$ concentrations on the order of $3\times10^{-5}$ μg/ml.

4 Claims, No Drawings

ISOLATION AND STRUCTURAL ELUCIDATION OF HALISTATIN 3

This research was funded in part by Outstanding Investigator Grant CA 44344-01A1-06 awarded by the National Cancer Institute, DHHS. The United States government may have certain rights to this invention.

This invention relates generally to the field of agents which may be potentially useful in the field of cancer chemotherapy. More particularly, this invention relates to the discovery and isolation of a new and novel polyether macrolide, which has been shown to be cytostatic to human cancer in vitro, and is denominated herein as "Halistatin 3".

BACKGROUND OF THE INVENTION

The present invention is a continuation of ongoing research conducted by the Cancer Research Institute ("CRI") at Arizona State University, Tempe, Ariz. The essential thrust of the research at the CRI has been to source, isolate, elucidate and ultimately synthesize new compounds from marine sources which during their evolution have exhibited an innate ability to avoid/resist carcinoma disease.

As that project evolved, CRI devised a system of naming the new compounds using, in most part, the organism in which the new compound was first detected and from which the compound was extracted. Additional compounds are added to a series by the addition of an ascending cardinal number to the root word. Specific nomenclature is adopted because of a common source or because, when a multiple source is discovered, because of generic structural kinship to a previously named substance.

Thus, in the present invention, the novel compound disclosed herein is denominated "Halistatin 3" even though it is extracted from Phakellia sp. because it is more closely related to previously discovered Halistatins than it is to the Phakellistatins.

Thus, several compounds which may be useful in the treatment of one or more neoplastic diseases through chemotherapy have already been isolated from the Western Pacific Ocean marine sponge Phakellia sp. These compounds include the cyclic heptapeptide previously denominated as phakellistatin 4, and several decapeptides.

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in their physical appearance during nearly 500 million years, suggesting a very effective chemical evolution in response to changing environmental conditions for at least the time period under consideration. Some recognition of the potential for utilizing biologically potent marine animal constituents was recorded in Egypt about 2,700 B.C., and by 200 B.C. sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute at Ariz. State University, Tempe, Arizona where five members of these remarkable anticancer drug candidates are either now in human clinical trial or preclinical development.

As is well known to those presently engaged in medical research, the time between the isolation of a promising new compound and its availability in the market place takes several years in the best case and can take several decades when an entity to finance the tortuous regulatory trail is slow to appear. Consequently, industry, in association with the government, has devised a number of qualifying tests which serve two purposes. One purpose is to eliminate those substances whose results in the qualifiers unequivocally demonstrate that the further expenditure of funds on developing those substances would be economically counterproductive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such corroborative data approaches Ten Million Dollars ($10,000,000 U.S.) per substance. Basic economics dictate that such an investment will not be made unless there is a reasonable opportunity to recover it. This opportunity can only be provided through patent protection. Absent such protection, there will be no incentive and hence no investment, and the advances in such life saving drugs will stop.

Only two hundred years ago, many diseases ravaged humankind. Many of these diseases have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting all anti-cancer research. To establish whether a substance has anti-cancer activity, NCI has established a variety of protocols, one of which involves testing the candidate substance against a cell line panel containing 60 human tumor cell lines. This protocol has been verified, and is generally accepted throughout the scientific community. This protocol and the established statistical means of evaluating the results obtained therefrom, have been fully described in the literature (See e.g., *Principles& Practice of Oncology*, PPO Updates, Volume 3, Number 10, October 1989, by Michael R. Boyd, M.D., Ph.D.) which is incorporated herein by this reference thereto. The statistical analysis of the values obtained is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al.

which is likewise incorporated herein by this reference thereto. Neither will be repeated herein.

The Constitution of the United States (Art. 1, Sec. 8) authorizes Congress to establish the United States Patent and Trademark Office (USPTO) to promote scientific advancement. In order for this obligation to be fully met, the USPTO must accept current medical and scientific realities in the area of medical research in order to fulfill the obligations placed upon it by the Constitution of the United States.

The Framers of the Constitution meant to advance scientific advancement. Cells are alive. The impairment of human tumor cell growth is utility. The sole right obtained from the grant of a letters patent is that of preventing others from exploiting the subject matter of the patent. The recognition of antineoplastic activity as utility can aid research in the United States, and prevent the citizens of the United States from being held hostage by foreign governments or foreign corporations, if such research is no longer viable in the United States.

A major component of vigorous efforts for over two decades has been directed at marine sponge antineoplastic and/or cytotoxic biosynthetic products. A number of unusual polyether macrolides, peptides and heterocyclic compounds have been uncovered. These efforts included the now disclosed isolation and structural elucidation of a new polyether macrolide, herein denominated "Halistatin 3".

BRIEF SUMMARY OF THE INVENTION

To date, many promising compounds have been developed from marine animals in general, and in particular Porifera indigenous to tropical areas. This is, in part, believed to be due to the lack of natural defenses possessed by such organisms, which requires them to protect themselves biochemically. Additionally, such organisms generally have extremely low incidences of neoplastic diseases.

Among those antineoplastic substances extracted from marine organisms, one notable group of compounds is the polyether macrolides. Such organisms include both sea hares and marine sponges.

Earlier existing members of the polyether macrolide series include bryostatin 1, halichondrin B and halistatin 1. The clinically promising results of bryostatin 1, and the selection of halichondrin B and halistatin 1, suggested the reexamination of previously collected productive organisms for previously undiscovered P388 active trace constituents.

Such an examination led to the discovery of halistatin 3 as a trace constituent of the orange Phakellia sp. (class Demospongiae, Order Axinellida, family Axinellidae) previously collected (1986-6) in the Federated State of Micronesia (Chuuk). It inhibited both the P388 leukemia cell line and selected brain, lung, colon, ovarian, renal, and melanoma type cancer cell lines with $ED_{50}/GI_{50}$ concentrations on the order of $3 \times 10^{-5}$ µg/ml.

Additionally, halistatin 1, halichondrin B and homohalichondrin B were also extracted as trace constituents of Phakellia sp. The yields for these compounds were on the order of $10^{-7}$–$10^{-8}$%.

DESCRIPTION OF THE PREFERRED EMBODIMENT

The importance of the subject invention is demonstrated by the pharmacological effects of the compounds disclosed herein. Accordingly, a brief explanation of the statistical measures employed in evaluating this activity is appropriate.

The following measures are used to express drug activity by giving the drug dose which reduces cell growth to a specified percentage of growth: $ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

Total Growth Inhibition ("TGI"), is the drug dose needed to yield zero percent growth, i.e., just as many cells at the end of the experiment as were present in the beginning. Whether just as many cells were killed as were produced (steady state), or no growth occurred (total inhibition), cannot be distinguished.

Lethal Concentration 50% ("$LC_{50}$"), is the drug concentration which reduces growth to −50%, i.e., removes half of the cells originally present at the beginning of the experiment.

Each drug is tested at five (5) doses: 100-10-1-0.1-0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

In determining "Percent of Growth", cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

|  | EXAMPLE: |
|---|---|
|  | Baseline Count =20 |
|  | Control Count =200 |
|  | (10-Fold Growth) |
| 100% Growth =Control Growth | 100% Growth =200 |
| 50% Growth =$T_{zero}$ + | 50% Growth =110 |
| Control − $T_{zero}$/2 |  |
| 0% Growth =$T_{zero}$ | 0% Growth =20 |
| −50% Growth =$T_{zero}$/2 | −50% Growth =10 |

The structures of halistatin 1, halichondrin B, and halistatin 3, are as set forth below:

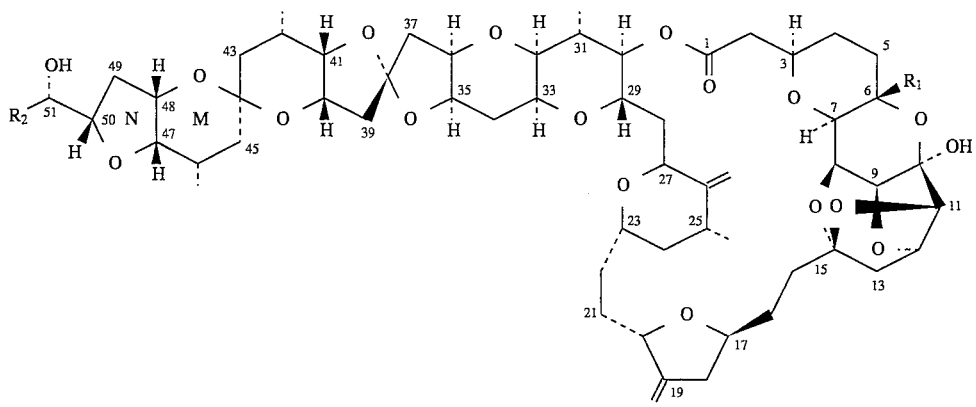

1a, $R_1$ =OH, $R_2$ =$CH_2CH(OH)CH_2OH$, Halistatin 1
1b, $R_1$ =H, $R_2$ =$CH_2CH(OH)CH_2OH$, Halichondrin B
1c, $R_1$ =H, $R_2$ =$CH_2CH_2CH(OH)CH_2OH$, Halistatin 3

The in vitro activity of halistatin 1 and halichondrin B are well known in the art and need not be repeated here. As is well known, both halistatin 1 and halichondrin B have been selected by the United States National Cancer Institute (NCI) for pre-clinical development.

Halistatin 3 has demonstrated the following in vitro activity, as shown in Table I below.

TABLE I

| Cell Line | | Concentration in μg/ml to achieve |
|---|---|---|
| Line | Cancer Type | $ED_{50}$ or $GI_{50}$ (× $10^{-5}$) |
| P388 | Leukemia | 3.5 |
| SF 295 | Brain | 3.5 |
| NCI 460 | Lung | 2.5 |
| KM 2062 | Colon | 5.1 |
| OVCAR-3 | Ovarian | 1.3 |
| A 498 | Renal | 5.6 |
| SK-MEL 5 | Melanoma | 2.5 |

These values are statistically indistinguishable.

The active ingredients were extracted in the following manner.

The earlier mentioned 500 kg, wet weight, collection of Phakellia sp. accomplished in 1987, was extracted with methanol followed by dichloromethanemethanol. The extracts were then assayed for P388 activity.

The P388 active dichloromethane fraction prepared from the extracts was separated by a sequence of size exclusion and partion chromatographic steps employing a SEPHADEX LH-20. Final isolation and purification was eventually realized by a combination of SEPHADEX LH-20 partition chromatography (hexane-dichloromethane-methanol, 5:1:1) and C-8 reversed-phase HPLC (2-propanol-water, 3:7) to afford the new cancer cell growth inhibiting macrolide designated halistatin 3 (1c, 1.9 mg, $3.8×10^{-8}\%$): m.p. 185°–187° C.; $[α]_D^{25}$ –62° (c=0.045, $CH_3OH$); UV ($CH_3OH$) $λ_{max}$ 201.0 nm (ε8000).

Structural elucidation of halistatin 3 was achieved by a combination of 2D NMR, FABMS and HRFABMS analyses. The FAB mass spectrum showed a quasi-molecular ion $[M+Na]^+$ at m/z 1147.6. The high resolution mass measurements established the molecular formula as $C_{61}H_{88}O_{19}$ from the molecular ion at m/z 1147.5771 (Δ –4.1 ppm) for $[M+Na]^+$. This suggested the presence of one additional methylene group than is found in halichondrin B (1b) and was confirmed by the similarities between the $^1$H-NMR and $^{13}$C-NMR spectrum of halistatin 3 and halichondrin B. The $^1$H-NMR spectrum of pyran 1c displayed four secondary methyls at δ0.95 (d, 7.0 Hz), 0.99 (d, 7.0 Hz), 1.05 (d, 7.5 Hz), and 1.09 (d, 6.5 Hz) characteristic of halichondrins/halistatins. The APT and HMQC spectra established the presence of four methyl, twenty two methylene (two exocyclic), twenty nine methine and six quaternary carbons, again indicating one more methylene than halichondrin B. Importantly, the NMR data established that halistatin 3, from rings A to M (the left terminal tetrahydropyran ring), was identical to that of halichondrin B (1b), including the unique tricyclic halipyran ring system. The only differences observed were in the left terminal ring (N) and side-chain of the molecule. Thus, we focused on the structure beyond the M ring of halistatin 3. Since unsaturation equivalents from the molecular formula required only one more ring in the system (i.e., N), the additional methylene group would have to be inserted either in the N ring or in the side-chain. Analyses of COSY, TOCSY, and HMQC spectra revealed the partial structure —CH(O)—CH(O)—$CH_2$— CH(O)—CH(O)—$CH_2$—$CH_2$—CH(O)—$CH_2OH$. The N ring proton chemical shifts suggested a 5-membered rather than a 6-membered ring. A deuterium-induced shift experiment also supported the 5-membered N ring (Δ δ $CD_3OH$—$CD_3OD$: C-50, 0.019; C-51, 0.104). Therefore, the new methylene group was placed between the two hydroxymethines at C-51 and C-53 of halichondrin B.

Uemura and co-workers determined the halichondrin B stereochemistry at C-50 and C-51 based on its biosynthetic relationship to norhalichondrin A (structure by X-ray crystal structure analysis) isolated from the same sponge (Halichondrin okadai) and the configuration assignments were later confirmed by total synthesis. Since we did not isolate any nor-series representatives from the Micronesian Phakellia sp., the stereochemistry of the halistatin 3 side-chain was further examined by high field $^1$H-NMR analysis. The coupling constants corresponding to H-47 (t, 2.5 Hz) indicated cis-fused M and N rings as in halichondrin B. Examination of results from decoupling experiments, in combination with $^1$H-$^1$H COSY and $^1$H J-resolved spectral analyses revealed the coupling patterns and coupling constants shown below in Table 1. The absence of coupling between H-48 and H-49α suggested the dihedral angle to be 90°. The coupling constant between H-50 and H-49α proved to be 3.0 Hz, while the coupling constant between H-50 and H-49β was 9.2 Hz. A study of molecular models using these coupling constants revealed that the configuration of H-50 was β. Since a plausible biosynthetic route to the halichondrin/halistatin family may involve cis-epoxides as intermediates in forming 5-and 6-membered cyclic ether rings typical of polyether natural products, the configuration of the hydroxyl group at C-51 is most likely α in relationship to H-50. Configuration of the hydroxyl group at C-54 will have to await an eventual X-ray crystal structure determination.

Based upon the foregoing, these compositions are believed useful in the treatment of one or more neoplastic diseases. For example, acute myelocytic leukemia, acute lymphocytic leukemia, malignant melanoma, adenocarcinoma of lung, neuroblastoma, small cell carcinoma of the lung, breast carcinoma, colon carcinoma, ovarian carcinoma, bladder carcinoma, and the like.

TABLE 1

The $^1$H and $^{13}$C NMR Chemical Shift Assignment for Halistatin 3 (1c) Determined in Methanol-$d_4$[a]

| Carbon no. | $^{13}$C(mult) | $^1$H(mult, J(Hz)) | Carbon no. | $^{13}$C(mult) | $^1$H(mult, J(Hz)) |
| --- | --- | --- | --- | --- | --- |
| C-1 | 172.86 (s) | | C-29 | 73.80 (d) | 4.23 (m) |
| C-2 | 41.26 (t) | 2.44 (dd, 17.5, 2.0) | C-30 | 77.43 (d) | 4.62 (dd, 7.5, 5.0) |
| | | 2.55 (dd, 17.5, 8.0) | C-31 | 37.54 (d) | 2.05 |
| C-3 | 74.94 (d) | 3.87 | 31-CH$_3$ | 15.86 (q) | 1.05 (d, 7.5) |
| C-4 | 31.88 (t) | 1.34, 1.72 | C-32 | 78.06 (d) | 3.21 (dd, 6.5, 4.5) |
| C-5 | 31.33 (t) | 1.40, 2.02 | C-33 | 65.75 (d) | 3.86 |
| C-6 | 69.64 (d) | 4.32 | C-34 | 30.88 (t) | 1.83, 2.06 |
| C-7 | 79.15 (d) | 2.97 (dd, 9.5, 2.0) | C-35 | 77.34 (d) | 4.06 |
| C-8 | 75.89 (d) | 4.29 | C-36 | 78.01 (d) | 4.09 |
| C-9 | 75.11 (d) | 4.11 | C-37 | 45.60 (t) | 2.02, 2.39 (dd, 13.5, 6.5) |
| C-10 | 77.94 (d) | 4.17 (t, 4.5) | C-38 | 114.86 (s) | |
| C-11 | 83.88 (d) | 4.59 (t, 4.5) | C-39 | 45.02 (t) | 2.33 |
| C-12 | 82.48 (d) | 4.69 (t, 4.5) | C-40 | 73.00 (d) | 4.03 |
| C-13 | 49.42 (t) | 1.98, 2.08 | C-41 | 80.83 (d) | 3.68 |
| C-14 | 111.31 (s) | | C-42 | 27.19 (d) | 2.26 |
| C-15 | 35.82 (t) | 1.59, 2.17 | 42-CH$_3$ | 18.18 (q) | 0.95 (d, 7.0) |
| C-16 | 29.46 (t) | 1.43, 2.18 | C-43 | 38.14 (t) | 1.27, 1.48 |
| C-17 | 76.36 (d) | 4.09 | C-44 | 98.31 (s) | |
| C-18 | 39.75 (t) | 2.31, 2.79 (m) | C-45 | 38.06 (t) | 1.38, 1.51 |
| C-19 | 153.22 (s) | | C-46 | 27.11 (d) | 2.32 |
| 19=CH$_2$ | 44.51 (d) | 5.01, 5.06 | 46-CH$_3$ | 18.37 (q) | 0.99 (d, 7.0) |
| C-20 | 76.15 (d) | 4.44 (br d, 10.5) | C-47 | 81.24 (d) | 3.35 (t, 2.5) |
| C-21 | 31.10 (t) | 1.36, 1.97 | C-48 | 73.46 (d) | 4.07 |
| C-22 | 33.06 (t) | 1.49, 1.67 | C-49 | 35.36 (t) | 2.00, 2.17 |
| C-23 | 75.42 (d) | 3.70 | C-50 | 82.19 (d) | 3.84 |
| C-24 | 44.95 (t) | 1.01, 1.72 | C-51 | 74.55 (d) | 3.60 |
| C-25 | 37.21 (d) | 2.29 | C-52 | 31.13 (t) | 1.46, 1.70 |
| 25-CH$_3$ | 18.42 (q) | 1.09 (d, 6.5) | C-53 | 30.65 (t) | 1.57 |
| C-26 | 153.35 (s) | | C-54 | 73.31 (d) | 3.59 |
| 26=CH$_2$ | 104.77 (t) | 4.80, 4.87 | C-55 | 67.48 (t) | 3.43 (dd, 11.0, 6.5) |
| C-27 | 75.11 (d) | 3.60 | | | 3.48 (dd, 11.0, 4.5) |
| C-28 | 37.85 (t) | 1.82, 2.25 | | | |

[a]$^1$H NMR 500 MHz; $^{13}$C NMR 126 MHz.

The structures of these compounds, halistatin 1, halichondrin B, and halistatin 3 are as shown below:

The dosage administered will be dependent upon the identity of the neoplastic disease; the type of host involved,

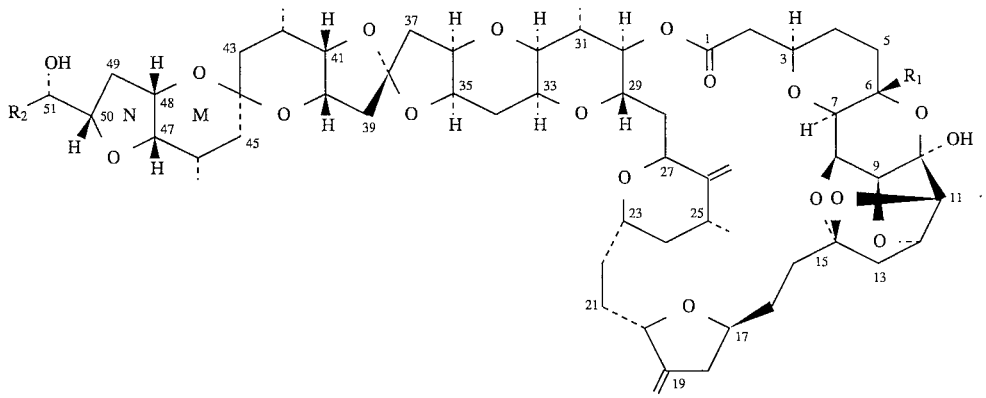

1a, R$_1$ =OH, R$_2$ =CH$_2$CH(OH)CH$_2$OH, Halistatin 1
1b, R$_1$ =H, R$_2$ =CH$_2$CH(OH)CH$_2$OH, Halichondrin B
1c, R$_1$ =H, R$_2$ =CH$_2$CH$_2$CH(OH)CH$_2$OH, Halistatin 3 including its age, health and weight; the kind of concurrent treatment, if any; the frequency of treatment and therapeutic ratio.

Illustratively, dosage levels of the administered active ingredients are: intravenous, 0.1 to about 2 mg/kg; intramuscular, 1 to about 5 mg/kg; orally, 5 to about 10 mg/kg; intranasal instillation, 5 to about 10 mg/kg; and aerosol, 5 to about 10 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies the compound designated herein as Halistatin 3.

COMPOSITION "A"

Hard-Gelatin Capsules

One thousand two-piece hard gelatin capsules for oral use, each capsule containing 0.2 mg of an active ingredient are prepared from the following types and amounts of ingredients:

| Active ingredient, micronized | 2.0 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 0.5, 25 and 50 mg amounts by substituting 5 g, 25 g and 50 g of an active ingredient for the 2.0 g used above.

COMPOSITION "B"

Soft Gelatin Capsules

One-piece soft gelatin capsules for oral use, each containing 0.2 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 0.2 mg of an active ingredient, are prepared from the following types and amounts of ingredients:

| Active ingredient, micronized | 2.0 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 0.25 mg and 1 mg amounts by substituting 2.5 g and 10 g of an active ingredient for the 2.0 g used above.

COMPOSITION "D"

Oral Suspension

One liter of an aqueous suspension for oral use, containing in each teaspoonful (5 ml) dose, 0.5 mg of an active ingredient, is prepared from the following types and amounts of ingredients:

| Active ingredient, micronized | 0.20 g |
|---|---|
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 0.30 mg of an active ingredient in each milliliter for treating a neoplastic disease, is prepared from the following types and amounts of ingredients:

| Active ingredient, micronized | 0.30 g |
|---|---|
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 0.2 mg of an active ingredient are prepared from the following types and amounts of ingredients:

| Active ingredient, micronized | 0.20 g |
|---|---|
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 0.20 mg of an active ingredient in each milliliter, is prepared from the following types and amounts of ingredients:

| | |
|---|---|
| Active ingredient, micronized | 0.20 g |
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 0.20 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 0.30 mg one to four times a day.

From the foregoing, it becomes readily apparent that a new and useful antineoplastic agent and new and useful antineoplastic preparations have been herein described and illustrated which fulfill the aforestated object in a remarkably unexpected fashion. It is, of course, understood that such modifications, alterations and adaptions as will readily occur to the artisan confronted with this disclosure are intended within the spirit of the present invention which is limited only by the scope of the claims appended hereto.

Accordingly, we claim the following:

1. A composition of matter comprising a substantially pure compound denominated "Halistatin 3" and having the structural formula set forth below:

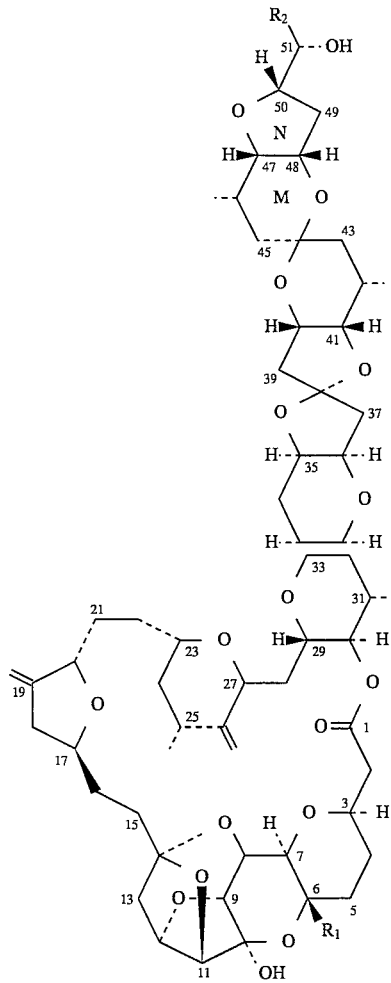

wherein $R_1=H$; and $R_2=CH_2CH_2CH(OH)CH_2OH$.

2. The composition of matter according to claim 1 further comprising a pharmaceutically acceptable carrier.

3. A method of treating a host afflicted with a neoplastic disease selected from the group consisting of P388 leukemia, SF295 brain cancer, NCI 460 lung cancer, KM 2062 colon cancer, OVCAR-3 ovarian cancer, A 498 renal cancer, and SK-MEL 5 melanoma comprising administering to said host an amount of halistatin 3 sufficient to reduce the percent growth of said neoplastic disease to 50% and having the structural formula:

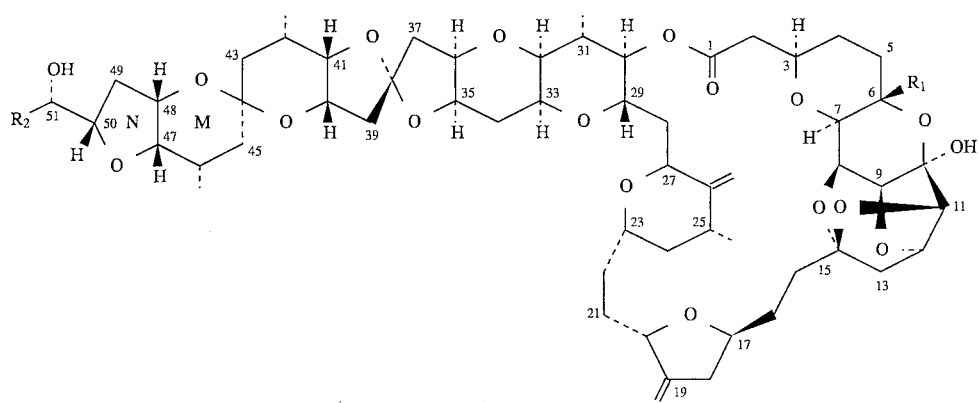
wherein:
$R_1$=H; and $R_2$=CH$_2$CH$_2$CH(OH)CH$_2$OH.
4. The method according to claim 3 wherein said halistatin 3 is administered in a pharmaceutically acceptable carrier.